United States Patent [19]

Evens et al.

[11] Patent Number: 5,078,493
[45] Date of Patent: Jan. 7, 1992

[54] FLOW CELL RESISTANT TO CORROSIVE ENVIRONMENTS FOR FIBER OPTIC SPECTROSCOPY

[75] Inventors: F. Monte Evens; Craig T. Barker, both of Ponca City; Charles R. Ray, Blackwell, all of Okla.

[73] Assignee: Conoco Inc., Ponca City, Okla.

[21] Appl. No.: 546,592

[22] Filed: Jun. 29, 1990

[51] Int. Cl.$^5$ .......................................... G01N 21/09
[52] U.S. Cl. .................................... 356/246; 250/343; 250/576
[58] Field of Search ............... 356/246, 410, 411, 440; 250/576

[56] References Cited

U.S. PATENT DOCUMENTS

| | | | |
|---|---|---|---|
| 3,177,706 | 4/1965 | Shuman et al. | 356/440 X |
| 3,573,470 | 4/1971 | Haley | 356/246 X |
| 4,008,397 | 2/1977 | Zdrodowski | 250/373 |
| 4,260,257 | 4/1981 | Neeley et al. | 356/246 |
| 4,540,280 | 9/1985 | Anderson et al. | 356/246 |
| 4,588,893 | 5/1986 | Vidrine et al. | 250/428 |
| 4,786,171 | 11/1988 | LeFebre et al. | 356/440 X |

Primary Examiner—Vincent P. McGraw
Attorney, Agent, or Firm—Cleveland R. Williams; Henry H. Huth

[57] ABSTRACT

A flow cell for use in highly corrosive environments is constructed from a cross union and contains opposing probes each with an external sapphire window which is sealed into a metal tube contained in each probe with melted glass and an optional plastic seal over the melted glass. Each portion of the cross union containing a probe has a right angle shoulder which abuts the end of the tube containing the sapphire window. An O-ring gasket is positioned between the right angle shoulder and tube end to form a tight cover over the glass seal when the probes are assembled in the flow cell, thereby protecting the glass seal and plastic seal from the corrosive environment.

18 Claims, 3 Drawing Sheets

FLOW CELL RESISTANT TO CORROSIVE ENVIRONMENTS FOR FIBER OPTIC SPECTROSCOPY

BACKGROUND OF THE INVENTION

In spectrophotometry, radiation from a source passes through a sample cell to a photodetector which measures the amount of radiation absorbed by the sample fluid in the cell. The output of the detector is a measure of absorbance at a particular wavelength of radiation. The quantitative presence of certain materials in the sample is identified by particular wavelengths characteristically absorbed by the materials. An important use of spectrophotometric detectors is in chromatography wherein the components of a chromatographic column are separated in a column and the radiation absorbance of the separated components are then measured by a spectrophotometric detector.

In such detectors, radiation transparent optical windows allow radiation from the source to pass through the cell to the detector. In a common spectrophotometric detector, radiation passes through an entrance window, through the cell in a direction parallel to the flow of sample fluid through the cell, and through an exit window to the detector. Flat windows or plano convex lenses typically have been used. U.S. Pat. No. 4,192,614 to deMey et al. shows a detector assembly with flat windows at the entrance and exit openings in the cell. A lens focuses the radiation in a pattern which converges in the cell.

Another type of commonly used detector has divergent optics with sample fluid flow across a substantially planar radiation field in the cell. Such crossflow cells are typified by the Milton Roy LDC microcell used in conjunction with the LDC Model 1204D spectoMonitor detector. Crossflow cells permit close coupling of the cell to the outlet end of a chromatographic column.

Another type of crossflow cell is available from Guided Wave Inc. of California. The Guided Wave cell comprises a standard ¼ inch cross union adapted to receive opposing fiber optic transmission probes. The probes contain an external sapphire window sealed into a ¼ inch metal tube. The metal tube also contains a suitable collimating lens. The tube which can be made from various materials including 316 stainless steel, Monel 400 or Hastelloy C276 alloys is sealed to the sapphire window with a soft glass frit. The glass frit is fused to prevent leaks between the sapphire window and the inner wall of the ¼ inch tube. An additional epoxy seal is used to coat the outer surface of the fused soft glass seal.

While the Guided Wave flow cell can be used in many services, it cannot be used in a hydrogen fluoride atmosphere or in a hydrogen fluoride, hydrogen chloride, chlorine atmosphere or in the presence of a strong caustic or in any other service where the epoxy and glass seal would be attacked by the materials flowing through the cell.

It is desirable to provide a cross union flow cell which can be used in such corrosive environments and in particular, in such environments at elevated temperatures.

THE PRIOR ART

U.S. Pat. No. 4,008,397, issued Feb. 15, 1977 discloses a fluorometer flow cell wherein the flow cell is constructed entirely of a light transparent polyfluoroethylene tubing. In addition, the flow cell contains a light source means, excitation filter means, cell holder means and photo detection means.

U.S. Pat. No. 4,260,257, issued Apr. 7, 1981 relates to a flow cell constructed by assembling together tubular components which are heated to form an integral flow cell member. The flow cell has a tubular body member, a debubbler unit and a tubular fluid outlet tower. The body member is made from quartz material and has an open ended bore therethrough which connects to a colorimeter. A pair of light transmitting quartz rods are positioned in the respective open ends of the bore to close them.

U.S. Pat. No. 4,540,280, issued Sept. 10, 1985 relates to a fiber optic thin-layer cell for use in spectrophotometric analysis of liquid or gaseous materials and a method of use, which consists of utilizing fiber optics in conjunction with low-volume, thin-layer cells.

U.S. Pat. No. 4,588,893, issued May 13, 1986 discloses a light-pipe flow cell suitable for use in analyzing high pressure fluids. The flow cell has a main support body with a gold light-pipe element mounted therein, two light transmissive window elements diametrically opposed to each other and a resilient sealing means mounted between each window element and the main support body. The flow cell is connected to an infrared spectrometer.

THE INVENTION

A flow cell which is suitable for use in corrosive environments comprising a cross union containing opposing fiber optic probes in which (1) each probe has a transparent light transmitting window extending from a tube contained within the probe. (2) the opening between the transparent light transmitting window and the probe is sealed with a sealing material which is attacked by the corrosive environment, and (3) an O-ring gasket resistant to the corrosive environment is positioned around the transparent light transmitting window adjacent the sealing material, said cross union having a right angle shoulder in two branches of the cross union which receive the opposing probes, said shoulders abutting the ends of the tubes extending outwardly from the transparent light transmitting windows which compresses the O-ring gasket when the probes are installed in the cross union, thereby shielding the sealing material from the corrosive environment.

DETAILED DESCRIPTION OF THE INVENTION

Figure 1:
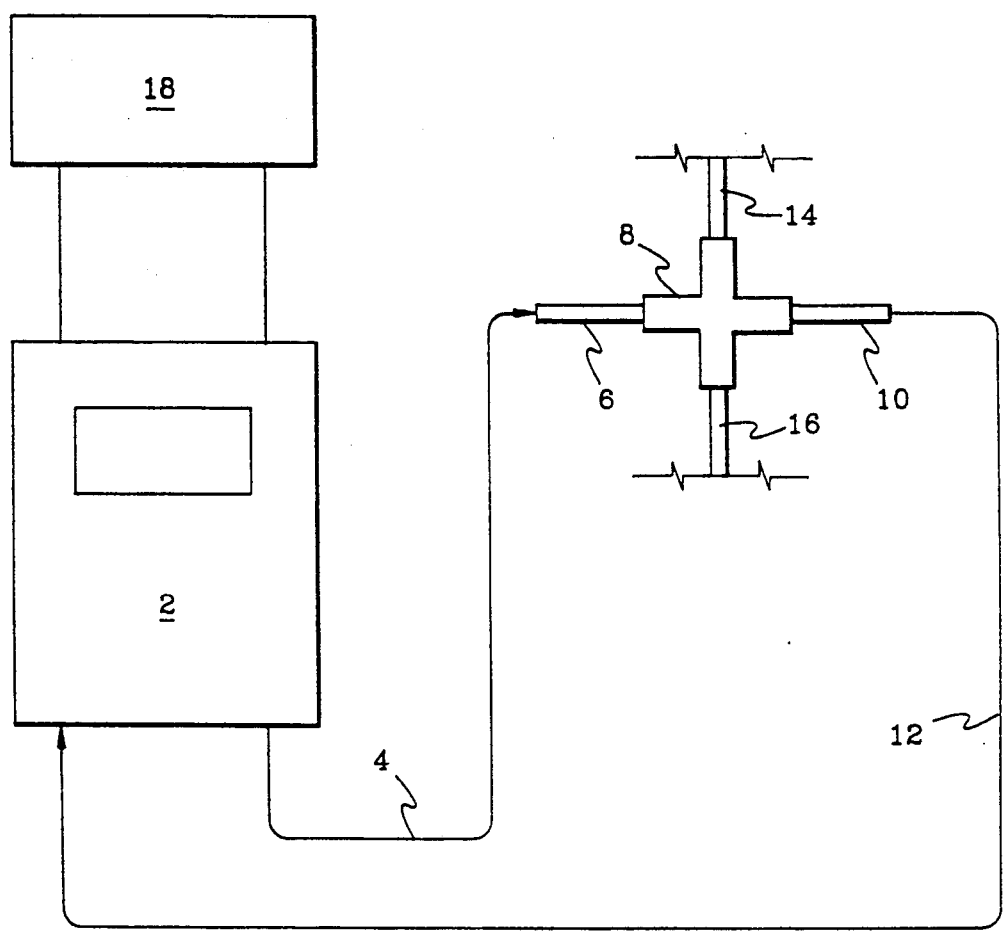
FIG. 1 is a schematic illustration of a fiber optic flow cell coupled to a spectrometer and a computer.

The invention is best described by reference to the drawings. FIG. 1 is a schematic diagram which illustrates the use of a cross union containing fiber optic probes in association with a spectrometer and a computer. Spectrometer 2 contains an appropriate radiation source which may be a tungsten-halogen lamp, deuterium arc. laser, or other suitable source. Source light is launched by focusing the radiation source on to a large diameter, single fiber cable 4 which then ducts the light to fiber optic probe 6 which is inserted in cross union 8. A sample, of which the absorbance is to be measured, is introduced to cross union 8 through line 14 and exits through line 16. The source light passes through probe 6 and the sample stream flowing through union 8, is received by a similar probe 10 and is returned to spectrometer 2 through optical fiber cable 12.

The sample passing through cross union 8 absorbs part of the light at a specific wavelength which is contained in the source light. When the source light returns to the spectrometer, the percentage of this wavelength absorbed is determined. Through the use of a suitable curve, relating concentration to wavelength absorbance for the sample, the concentration of the material being measured in the sample stream is determined. By use of computer 18 with an appropriate computer program, the output of the spectrometer is processed and periodically provides the desired concentration printout or reading. In this manner, changes in concentration of the flowing sample may be determined with desired frequency and operating conditions or parameters may be adjusted in response to such changes in concentration.

Figure 2:
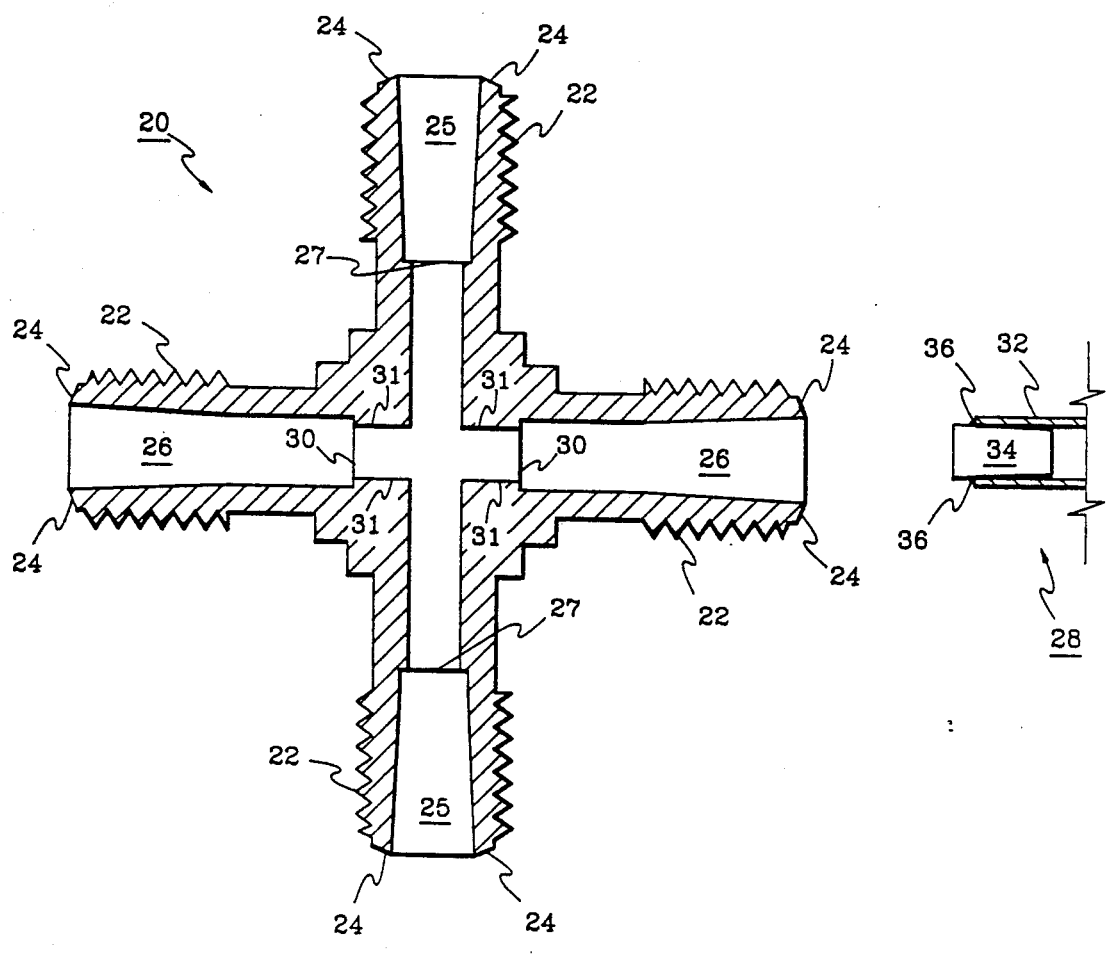
FIG. 2 is an illustration in cross-section of a cross union modified in accordance with the invention, adapted to receive a fiber optic probe, a portion of which is also shown in cross-section.

FIG. 2 illustrates in cross section a standard cross union 20 which has been modified in accordance with the invention. The sample of which the absorbance is to be measured is introduced to one of opposing passageways 25 and leaves the cross union through the other passageway. At the end of each passageway, is a threaded section 22 which contains a beveled portion 24. A ring ferrule made of Teflon ® or other suitable material is used to provide a pressure seal when the sample feed line (not shown) is attached by a suitable pressure fitting to the cross union. A similar attachment is made at the other end of the other passageway 25 to provide for exit of the sample from the cross union.

Each passageway in cross union 20 contains an abutment or shoulder which is shown at 27 in passageways 25. In an ordinary tubing assembly, the purpose of this shoulder is to set the distance at which tubing is inserted into the cross union. For example, with a ¼ inch cross union standard ¼ inch tubing, when inserted in the union, would butt up against shoulder 27. Without this shoulder, it would be necessary to measure the ¼ inch tubing each time connections to a cross union are made. Without such a measurement, the tubing might be inserted into the cross union so far that flow through the opposing branches of the cross union would be obstructed. As stated above, the sample feed and exit lines are pressure sealed by ring ferrules located at beveled portions 24. In a standard cross union assembly, sealing is not provided for at the internal abutment of the tubing end and the cross union, but only at beveled portions 24.

The opposing arms 26 of the cross union are adapted to receive fiber optic probes, one of which is designated in part by 28. The end portion of fiber optic probe 28 which is inserted in cross union 20 comprises a tube 32 in to which there is inserted a transparent, light transmitting optical window made of sapphire or other suitable material. The space between window 34 and tube 32 is sealed with a suitable sealing material such as melted glass 36. An additional sealing material (not shown) e.g. a plastic material such as epoxy may be applied over the glass sealing. For ease of installation, window 34 is slightly tapered in the the direction in which it is placed in tube 32.

In passages 26 of cross union 20, the portion of the cross union which terminates in shoulders 27 is machined or drilled out to form a new, substantially right angle shoulder 30. The inner portion 31 of cross union 20 adjacent shoulder 30 is of a diameter slightly greater than window 34 so that when the fiber optic probe 28 is inserted in passage 26, shoulder 30 abuts the end portion of tubing 32 which extends outwardly from window 34. The position of the shoulder (including the compressed O-ring described in the discussion of FIG. 3) sets the optical path length of the probe.

The cross unions used in the flow cells of the invention are usually ¼ inch or ½ inch in size. However, larger cross unions may be used with appropriately sized probes. The transparent light transmitting window used in the fiber optic probe is usually made of sapphire, however, other materials such as diamond may also be used. Under milder corrosive conditions, other materials such as quartz may also be employed. The transparent light transmitting material is sealed in the probe tube with a sealing material which provides an effective seal at the temperature of the sample being measured. Usually, fused glass is preferred, however, at lower temperatures, polymeric materials such as epoxys may be used.

Figure 3:
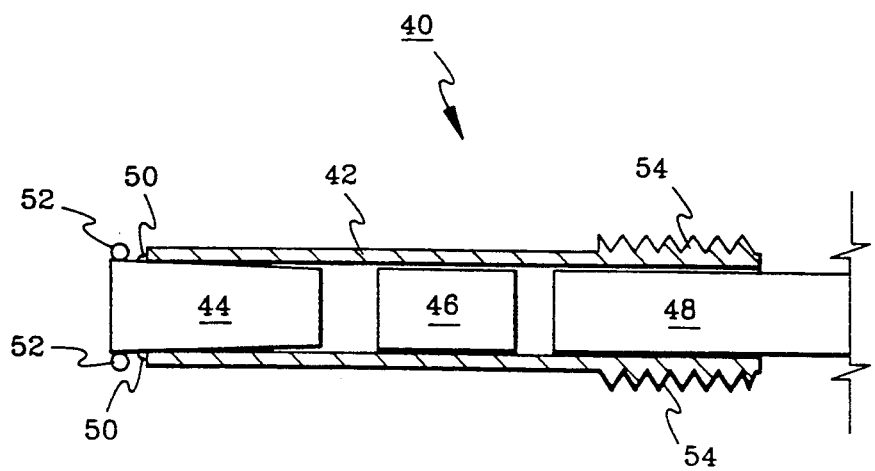
FIG. 3 is a more detailed schematic illustration of a fiber optic probe suitable for installation in the modified cross union of FIG. 2.

FIG. 3 shows a more detailed schematic in cross section of a fiber optic probe. In this figure, the transparent light transmitting window 44 is inserted in tube 42. Adjacent window 44 is a collimating lens which may be made of silica or other suitable material. Adjacent the collimating lens is an optical fiber cable 48 through which light is transmitted to collimating lens 46. Light leaving the collimating lens passes through window 44 and through the sample to be measured. The opening between tube 42 and light transmitting window 44 is sealed with a suitable sealing material 50. An O-ring gasket 52 is placed around light transmitting window 44. When the probe is inserted into modified cross union 20 (FIG. 2), the O-ring is compressed between the end of tube 42 and right angle shoulder 30 described in the discussion of FIG. 2. Compression of O-ring 52 provides complete coverage of seal 50 thereby eliminating exposure of seal 50 to any corrosive material in the sample being measured. Probe 40 is affixed to cross union 20 by a nut and ferrule assembly (not shown) of either the two-piece or one-piece type. Tube 42 is threaded at 54 to receive a fitting by which optical fiber 48 is affixed to tube 42.

The O-ring used in the modified cross union of the invention serves two important functions. Primarily it protects the seal between the transparent light transmitting window and the probe tube from the corrosive sample. It also prevents damage to the probe in the event that the seal were not totally effective and allowed leakage of the corrosive sample into the probe. The O-ring may be made of a variety of materials depending on the particular chemical or chemicals contained in the samples being measured. In an atmosphere of hydrofluoric acid, fluoro-elastomers such as Kalrez ® are used. Various chloroprene polymers may also be used in this service. For less corrosive atmospheres and for lower temperatures, other materials such as silicone rubber, neoprene, etc. may be used for the O-ring.

Effective coverage of seal 50 by O-ring 52 is obtained by hand pressure when the flow cell is assembled. However, if desired, a measured pressure on the O-ring may be provided by a suitable apparatus constructed to grip both the cross union and probe during assembly.

In samples containing hydrofluoric acid, the cross union is usually constructed of high nickel steel alloys such as Hastelloy C276. Monel may also be used with hydrogen fluoride and hydrogen chloride at lower temperatures. Depending on the type of corrosive atmosphere, stainless steels such as 316 stainless steel may also be used in the construction of the cross union.

In the construction of the probe, the transparent light transmitting window usually extends out from the probe tubing for a distance of about ⅛ inch to about ¼ inch. The minimum length of extension will be the width of the O-ring. The probes may be installed in a cross union at any distance up to 2 or 4 centimeters apart in a ¼ inch or ½ inch cross union, respectively. Usually the probes will be spaced from about ½ to 2 centimeters apart. As stated previously, proper location of shoulders 30 (in FIG. 2) sets the optical path length of the probe. This eliminates time consuming measurements when the probe is removed from the cross union and then reassembled. Operations of the probe at more than one optical path length may be provided by the use of several cross unions in each of which shoulders 30 are located at different points in passageway 26.

The following examples are presented in illustration of the invention.

EXAMPLE 1

A ¼ inch flow cell modified as shown In FIG. 2 was constructed from a ¼ inch, 316 stainless steel cross union. A machine dummy probe was installed in the cross union and tested at 1000 psi for 30 minutes. No leaks were observed from the cross union and there was no movement of the probe.

EXAMPLE 2

A ¼ inch modified flow cell constructed of Hastelloy C276 was assembled with two fiber optic probes. The O-rings used in the probe were made of Kalrez ® fluoro-elastomer which is resistant to highly corrosive materials such as hydrogen fluoride, hydrogen chloride, chlorine, caustics and the like. Teflon ® ferrules were used in the fittings employed for attaching the probes to the modified cross union.

Optical performance tests for the assembled flow cell were carried out with a Guided Wave Inc. model 200 analyzer (spectrometer). All of the tests showed that the two transmission probes were in optical alignment and that the flow cell transmitted sufficient light intensity to produce an acceptable signal/noise value for quantitative spectrophotometric measurements.

Figure 4:
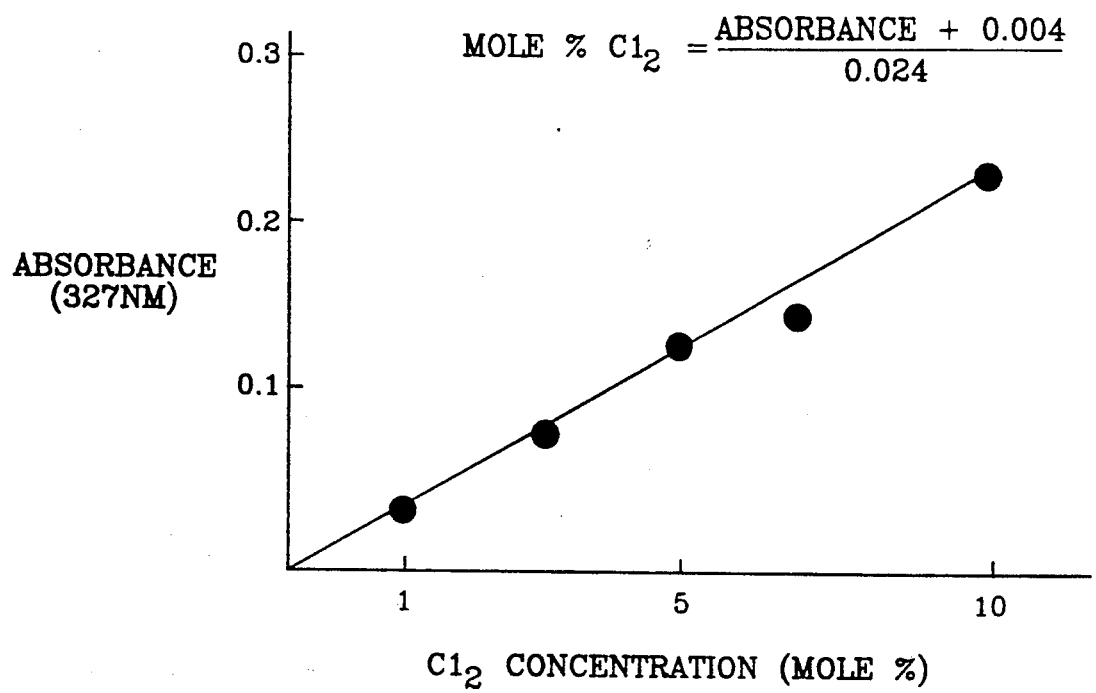
FIG. 4 is a plot showing the relationship between chlorine concentration and peak absorbance measured at 327 nanometers.

The assembled flow cell was tested for analytical performance using commercial gas mixtures of chlorine and nitrogen. All tests were conducted at atmospheric pressure and ambient temperature. FIG. 4 shows the analytical calibration produced from these tests. The calibration shows the relation between the peak absorbance measured at 327 nanometers and the chlorine concentration flowing through the flow cell. A short term stability test using a 6.9 percent chlorine standard flowing at ambient temperature and at atmospheric pressure showed acceptable analytical performance for an uninterrupted four hour interval.

EXAMPLE 3

Several tests were carried out with the assembled flow cell of Example 2 installed "on line" as a part of a laboratory reactor system. The operating conditions for the tests were 40° C. and 20 psig. The system was exposed to a continuous flow of hydrogen fluoride, hydrogen chloride and chlorine and various mixtures of these components according to the operating flow conditions used with the reactor. At the same time, spectrophotometric measurements to monitor the chlorine content in the gas stream were continuously completed using 20 meter fiber optic cables and the Guide Wave Inc. Model 200 analyzer. The tests were conducted for seventeen days of continuous operation.

The next test was a thirty day static measurement using chlorine gas at 40 psig and 200° C. The pressure in the cell was adjusted as needed to maintain the 40 psig condition. A continuous measurement of the chlorine content in the cell was recorded during the test. Because of the high temperature used in this test, a graphite ferrule was substituted for the Teflon ® ferrule used in the flow cell of Example 2.

Visual inspections of the disassembled flow cell were made at the conclusion of each of the tests in this example. These inspections showed no evidence of corrosion of the flow cell and no indication of abrasive or etching deterioration of the soft glass seal surrounding the sapphire window. The sapphire window was also unaffected by the compounds used in the test. These observations were also confirmed by optical microscopy examinations. It was discovered that the epoxy coating on the soft glass seal was thermally volatilized from the probes during the first 200° C. test. It was verified that the epoxy used in the manufacture of the flow cell was not rated for long time use at this temperature.

EXAMPLE 4

Pilot plant tests were carried out by installing a ¼ inch modified Hastellory C276 flow cell "on line" as a part of a research pilot plant. The location selected was adjacent to a commercial. non-dispersive UV process analyzer. Installation was set so that the process gases under examination flowed in series through the modified ¼ inch fiber optic flow cell then on through the conventional gas absorption cell in the process analyzer. The 20 meter fiber cables used for the tests were run from the flow cell to the Guided Wave Inc. Model 200 analyzer located in a laboratory control area adjacent to the pilot plant.

Preliminary tests were made for thirty days using a static chlorine/nitrogen blend at 150° C. and 40 psig. There was no loss of optical performance during this test. Analytical calibrations of the flow cell system were next made with chlorine and nitrogen gas mixtures flowing through the cell at 150° C. and at incremental pressures of 100, 150, and 180 psig. The chlorine concentration range of 0 to 10 mole percent was examined. The data showed that the fiber optic system performed equal to if not superior to the commercial process analyzer.

The fiber optic flow cell system was used to monitor the chlorine content in the process gas flow during pilot plant test runs. During these tests, the flow cell was subjected to various mixtures of hydrogen fluoride, hydrogen chloride, and chlorine gas mixtures. Operating conditions at the flow cell were 150° C. and 180 psig.

Following the above operations, the flow cell was disassembled for visual inspection. There was no indication of corrosion of the flow cell and no evidence of abrasive or etching deterioration of the soft glass seal surrounding the sapphire window. The sapphire window was the same in appearance as observed at the start of the test. These observations were also verified by optical microscopy examinations.

EXAMPLE 5

A modified ¼ inch stainless steel fiber optic flow cell was installed in a laboratory circulation loop. A pump was used to circulate 2.0 molar potassium hydroxide solution (11 wt. %) from a 500 milliliter reservoir through the cell and back to the reservoir. The temperature of the system was ambient which was 20° C.

The solution was circulated for about one month. Disassembly of the flow cell indicated no noticeable deterioration in the flow cell or the O-ring sealing assembly. The sapphire window was in the same condition as at the start of the test.

The foregoing examples illustrate that it is possible through use of the modified fiber optic flow cell of the invention to monitor process streams when highly corrosive materials such as hydrogen fluoride, hydrogen chloride, chlorine or caustic are present both at ambient and elevated temperatures without deterioration of the sealing material between the sapphire window and the tube holding such window.

The apparatus of the invention has been described in conjunction with the modification of a standard cross union. While such an arrangement is preferred because of the commercial availability of such unions, it is also within the scope of the invention to manufacture a union having the shoulders built in and located to provide the desired optical path for the installed probes.

While certain embodiments and details have been shown for the purpose of illustrating the present invention, it will be apparent to those skilled in the art that various changes and modifications may be made herein without departing from the spirit or scope of the invention.

We claim:

1. A flow cell suitable for use in a corrosive environment which comprises:
   (a) a cross union housing containing diametrically opposed fiber optic probes, each probe having a light-transmitting, transparent window extending from a tube contained in each probe;
   (b) an opening between each tube and light-transmitting window, said opening being sealed with a sealing material which is attacked by the corrosive environment;
   (c) a right angle shoulder in each section of the cross union housing which contains a fiber optics probe, said shoulder abutting the end of the tube extending outwardly from the light-transmitting, transparent window; and
   (d) in each such section a corrosive-resistant, O-ring gasket compressively positioned between the end of the tube and the right angle of said cross union housing, thereby protecting the sealing material from the corrosive environment.

2. The flow cell of claim 1, wherein the light-transmitting, transparent window is sapphire.

3. The flow cell of claim 1, wherein the sealing material is glass.

4. The flow cell of claim 1, wherein the sealing material is melted glass coated with epoxy plastic.

5. The flow cell of claim 1, wherein the corrosive-resistant, O-ring gasket is constructed of a material selected from the group consisting of a fluoro-elastomer, a chloroprene polymer, silicone rubber and neophrene and mixtures thereof.

6. The flow cell of claim 1, including means for receiving and discharging a sample into and out of said flow cell.

7. The flow cell of claim 1, including means for receiving or sending a signal to or from an infrared spectrometer and a computer.

8. A flow cell which contains fiber optic probes suitable for use in a corrosive environment which comprises;
   (a) a cross union housing containing two opposing fiber optic probes, each probe having a light-transmitting, transparent window extending from a tube contained in each probe;
   (b) an opening between each tube and light-transmitting window, wherein said opening is sealed with melted glass, which is attacked by the corrosive environment;
   (c) a right angle shoulder in each section of the cross union housing which contains a probe, said shoulder abutting the end of the tube extending outwardly from the light-transmitting, transparent window; and
   (d) in each such section a corrosive-resistant, O-ring gasket compressively positioned between the end of the tube and the right angle shoulder of said cross union housing, thereby protecting the melted glass from the corrosive environment.

9. The flow cell according to claim 8, wherein the light-transmitting window is sapphire.

10. The flow cell according to claim 8, wherein the melted glass of step (b) is coated with an epoxy plastic.

11. The flow cell according to claim 8, wherein the O-ring gasket of step (d) is constructed of a material selected from the group consisting of a fluoro-elastomer, a chloroprene polymer, silicone rubber and neoprene and mixtures thereof.

12. The flow cell of claim 8, including means for receiving and discharging a sample into and out of said flow cell.

13. The flow cell of claim 8, including means for receiving or sending a signal from the fiber optic probes to or from an infrared spectrometer and a computer.

14. A flow cell suitable for use in a corrosive environment which comprises:
   (a) a corrosive-resistant, cross union housing containing two opposing fiber optic probes in two opposing sections of the cross union housing, each of said probes containing a light-transmitting, sapphire window extending from a tube contained in the probe;
   (b) an opening between the sapphire window and tube, which is sealed with melted glass which is attacked by the corrosive environment;
   (c) a right angle shoulder in each section of the cross union housing which contains a probe, said shoulder abutting the end of the tube extending outwardly from the sapphire window; and
   (d) in each such section a corrosive-resistant, O-ring gasket compressively positioned between the end of the tube and the right angle shoulder of said cross union housing thereby protecting the melted glass from the corrosive environment.

15. The flow cell according to claim 14, wherein the melted glass of step (b) is coated with epoxy plastic.

16. The flow cell according to claim 14, wherein the O-ring gasket of step (d) is constructed of a material selected from the group consisting of a fluoro-elastomer, chloroprene polymer, silicone rubber and neoprene and mixtures thereof.

17. The flow cell according to claim 14, including means for connecting said flow cell to an infrared spectrometer and a computer.

18. The flow cell according to claim 14, including an entrance and an exit for a sample into and out of said cross union housing.

* * * * *